United States Patent [19]

Hall et al.

[11] Patent Number: 4,576,798
[45] Date of Patent: Mar. 18, 1986

[54] CONTACT LENS DISINFECTING UNIT

[75] Inventors: Henry B. Hall, Madison; Peter B. Hewes, Middlefield; Benjamin N. Moore, Haddam; Rosario Sanzaro, Durham, all of Conn.

[73] Assignee: Safeway Products, Inc., Middletown, Conn.

[21] Appl. No.: 506,312

[22] Filed: Jun. 21, 1983

[51] Int. Cl.[4] .............................................. A61L 2/18
[52] U.S. Cl. .................................. 422/105; 219/439; 219/441; 219/521; 422/300; 422/307
[58] Field of Search ............. 422/105, 109, 164, 292, 422/300, 302, 307; 219/322, 328, 386, 413, 430, 435, 439, 441, 462, 460, 494, 510, 516, 522, 530, 521, 531, 536; 99/329 R

[56] References Cited

U.S. PATENT DOCUMENTS

| | | | |
|---|---|---|---|
| 3,870,858 | 3/1975 | Schimke | 219/441 X |
| 4,044,226 | 8/1977 | Kadlecik et al. | 422/1 X |
| 4,158,126 | 6/1979 | Seitz | 422/307 X |
| 4,178,499 | 12/1979 | Bowen | 422/307 X |
| 4,270,039 | 5/1981 | Hauser | 219/430 X |
| 4,341,948 | 7/1982 | Sundstrom et al. | 422/307 |
| 4,341,949 | 7/1982 | Steiner et al. | 219/439 X |
| 4,379,965 | 4/1983 | Dounce et al. | 219/438 X |

Primary Examiner—Barry S. Richman
Assistant Examiner—William R. Johnson
Attorney, Agent, or Firm—Hayes & Reinsmith

[57] ABSTRACT

A contact lens disinfecting unit in which the lenses are immersed in a saline solution and heated to a predetermined minimum disinfecting temperature which is maintained for a predetermined period of time. The unit has a heating system which includes a PTC thermistor as a heating element sandwiched between metal heat distribution plates, and this heating system interacts with a manually resettable thermostat to control operation of the unit.

7 Claims, 4 Drawing Figures

CONTACT LENS DISINFECTING UNIT

BACKGROUND OF THE INVENTION

This invention relates to a disinfecting unit for contact lenses. More particularly, this invention relates to a disinfecting unit for soft lens contact lenses in which the lenses are immersed in a saline solution and heated at a predetermined temperature for a predetermined period of time to accomplish disinfection of the lenses.

Contact lenses are an increasingly popular alternative to eye glasses; and the so-called "soft" contact lenses have solved a number of problems which prevented some people from using contact lenses. It is well known that contact lenses in general, and soft lenses in particular, should be disinfected at regular intervals to prevent eye infection. Disinfecting units have been proposed in the past, but these units have drawbacks or deficiencies of one kind or another.

A known and typical method for disinfecting contact lenses is to immerse them in a saline solution which is then heated for a period of time. An important FDA requirement for disinfecting soft contact lenses is that the lenses be heated for a minimum period of ten minutes at 80° C. However, in attempting to meet this requirement, the problem is encountered of also limiting the maximum temperature to which the lenses are exposed to prevent overheating of the lenses and the promotion of heat aging.

SUMMARY OF THE INVENTION

The present invention presents novel and improved disinfecting apparatus which meets the objective and requirement of establishing a minimum disinfecting temperature and maintaining it for a minimum period of time, while also preventing overheating or overtemperature which would adversely affect the lenses.

In accordance with the present invention, a lens case which contains the contact lenses in a saline solution is housed in a heating cavity in the disinfecting unit. The heating cavity is isolated from the saline solution per se and does not physically contain the heating element.

The heating structure of the present invention consists of a PTC thermistor which is positioned in a plastic plate which is, in turn, sandwiched between a pair of metal, preferably aluminum, plates. The metal plates serve as both electrodes for the PTC thermistor and as heat distribution and heat sink elements. This sandwich assembly is positioned on the underside of the heating cavity. Voltage applied across the thermistor results in current flow and heat generation whereby heat is delivered to the heat sink plates for transfer to the lenses in the heating cavity. The thermistor has the characterisitic that its electrical resistance increases rapidly when a predetermined temperature is reached, so that current flow, and hence heat generation, are reduced. Thus, a temperature overshoot is avoided in the present invention. The unit of the present invention also has a manually resettable thermostat in the power supply circuit. This thermostat is set to shut off the power supply when the temperature of the heat generating subassembly reaches a predetermined temperature.

Bearing in mind that the heating requirements for disinfecting require a minimum soak of ten minutes after the disinfecting temperature has been reached, and also bearing in mind that a heating unit will tend to cool down once the heat supply is terminated, in the prior art a problem of overtemperature might be encountered if the thermostat cut off temperature were set high enough to provide the required heat for soaking; while the disinfecting temperature might not be retained for the required time period if the thermostat cut off temperature were set too low. This problem is avoided in the present invention by the thermistor heating element and the heat sink and heat distribution structure of the sandwich of metal and plastic plates. While the thermistor is functioning to supply heat, a quantity of residual heat is stored in the heat sink structure. This residual heat is delivered to the heating cavity after the thermostat cuts off the power supply. Thus, the heat sink structure serves as a residual heat supply to maintain the required minimum soak temperature for the required duration of soak time.

The characteristic of the thermistor wherein its electrical resistance increases with temperature is employed to create a structure in which a proper balance can be and is maintained between the temperature and quantity of heat in the heat sink structure, the temperature and quantity of heat delivered to the thermostat, and the temperature and heat quantity delivered to the heating cavity and lens case. The result achieved with the present invention is a novel and improved soft lens disinfecting unit in which the desired soak temperature is established and maintained for the desired soak period of time without adverse effects on the lenses. The disinfecting unit of the present invention can be operated at all common numeral voltages of from 100 V to 240 V ± 10% at ambient temperatures of from 5° C. to 40° C. Thus, the unit is universal in that it can serve a worldwide market merely by changing the power cord and the resistance of the indicating light.

BRIEF DESCRIPTION OF THE DRAWING

Referring now to the drawings, wherein like elements are numbered alike in the several FIGURES.

DESCRIPTION OF THE PREFERRED EMBODIMENT

Figure 1:
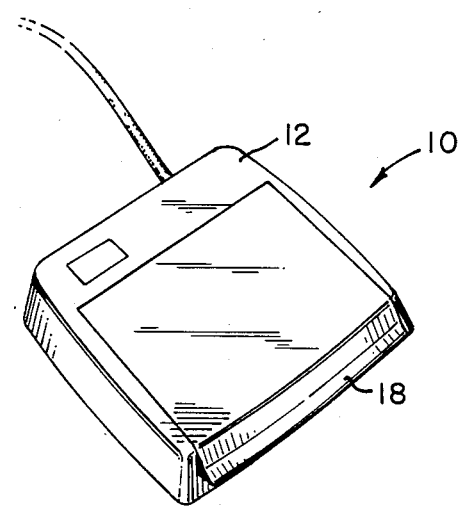
FIG. 1 is a perspective view of the disinfecting unit of the present invention.
Figure 2:
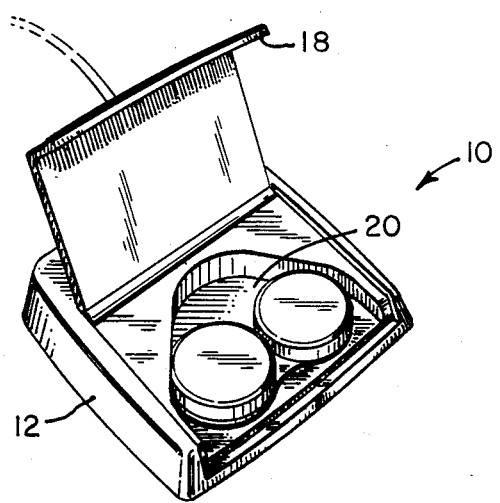
FIG. 2 is a perspective view similar to FIG. 1 showing the disinfecting unit with the cover opened and a lens case in place in the unit.
Figure 3:
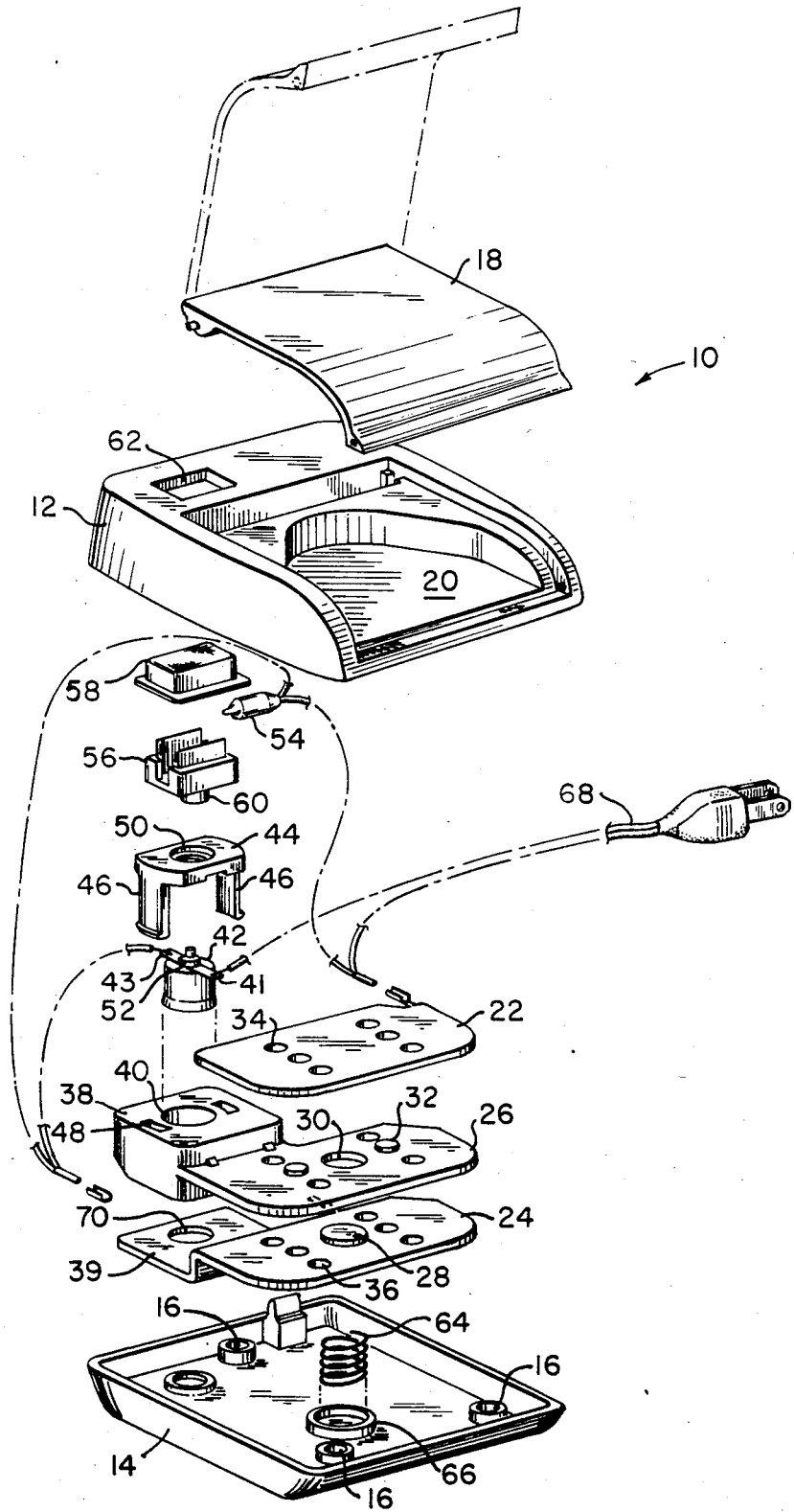
FIG. 3 is an exploded view showing, in detail, the elements and construction of the disinfecting unit of the present invention.

Referring to a joint consideration of FIGS. 1, 2 and 3, the disinfecting unit 10 has an upper housing 12 and a lower housing 14, both of which are made of high temperature thermoplastic materials which can withstand operating temperatures of 300° F. or higher. These upper and lower housings are molded elements, and they may be made from materials such as Union Carbide Ardel D-100 or DuPont Rynite FR530. In final assembly, the upper and lower housing elements are joined together by posts (not shown) which project from the underside of upper housing segment 12 into apertured bosses 16 in the lower housing and which are ultrasonically welded together. Upper housing segment 12 has a hinged lid or cover 18 which opens to expose a triangular shaped cavity in upper housing segment 12.

Cavity 20 is triangularly shaped so that it can accept either an oblong shaped lens case or a round lens case, those being the two general shapes of lens cases in widespread commercial use. One example of a contact lens case is shown positioned in cavity 20 in FIG. 2. When lid 18 is closed, as shown in FIG. 1, it snaps or locks into place, such as by the use of detents or similar conventional mechanism, so that positive force is required to open it. Since top housing element 12 is an integral molded element, cavity 20 provides an enclosed and isolated cavity which is mechanically and electrically isolated from the electrical components (to be described in more detail hereinafter) located between the upper and lower housing segments. This isolated cavity prevents leakage of saline solution from the lens case into any of the heating and electrical components within the interior of the unit.

Referring particularly to FIG. 3, the details of the heating element and control structure of the present invention are shown. The heating unit of the present invention includes a pair of aluminum plates 22 and 24 which are secured to and form a sandwiched structure about an intermediate separator or insulating plate 26. Spacer plate 26 may be a plastic material molded from the same plastic material from which the housing units are formed. A positive temperature coefficient (PTC) heater element (such as Q63100-P2442-A69 of Siemens Corporation) in the form of a cylindrical disk or wafer is located in a central opening 30 which passes completely through plastic spacer 26; and the opposite faces of PTC element 28 are in intimate contact with the inwardly facing surfaces of aluminum plates 22 and 24. The assembly or sandwich of the two aluminum plates and the separating plastic plate are intimately joined together by means of posts 32 which project from the upper and lower surfaces of plastic plate 26 and pass through mating openings 34 and 36 in the aluminum plates. The plates are assembled with the posts 32 passing through the respective holes 34 and 36, and the assembly is then ultrasonically staked to cause the exposed ends of the posts to mushroom over and lock the metal plates to the plastic plate, with the PTC heater element 28 being in position in through hole 30 and with its opposed surfaces in intimate engagement with the plates 22 and 24.

The PTC resistor heater element 28 (also known as a thermistor) is a semiconductive ceramic material with electrically conductive coatings on the upper and lower surfaces of the disk, which coatings are in contact with the aluminum plates 22 and 24. As will be discussed in more detail hereinafter, this PTC element functions as a self-limiting heating element in the present invention.

The heating unit structure of the present invention also includes a thermostat housing 38 in the form of an enlarged portion integrally formed with and extending from plastic separator plate 26. The bottom of housing 38 is in intimate contact with extension 39 of plate 24 for heat transfer from the plate to the housing. Thermostat housing 38 has a cylindrical recess 40 in which a thermostat element 42 having contacts 41 and 43 is housed. A retainer element 44 has projecting legs 46 which lock into mating openings 48 in thermostat housing 38 to securely hold the thermostat in place and urge it firmly against the bottom of the thermostat housing. Retainer 44 has a central opening 50 through which a reset button 52 of the thermostat projects. Thermostat 42 is a manually resettable snap action thermostat such as a Model 2455RM thermostat available from Elmwood Sensors Inc. or Therm-O-Disc Inc. Type 36TX06.

The unit also includes an indicating lamp 54 which is housed in a plastic housing 56 and which is visible through a transparent indicator cover 58 which mates with the top of housing 56. Housing 56 is above retainer 44, and housing 56 has a downward cylindrical projection 60 which passes through opening 50 and sits on top of reset button 52 of thermostat 42. The cylindrical projection 60 serves to deliver a reset force to reset the thermostat. When the unit is assembled, indicator cover 58 passes through and is retained in an appropriately shaped opening 62 in the upper surface of top housing element 12. In the operation of the device to reset the thermostat to arm the unit for operation, the operator would press on the top of cover 58 which would force the cover in housing 56 slightly downwardly whereby projection 60 would depress reset button 52 to close the contacts of thermostat 42 which would have been opened in the course of a previous operation of the unit.

When the unit is assembled, a coil spring 64 located on a boss 66 on the lower housing element 14 forces the sandwiched plate assembly upwardly so that the upper surface of aluminum plate 22 is pressed firmly against the underside of cavity 20 to be in firm physical and heat transfer contact with the underside of cavity 20. Spring 64 is directly beneath PTC heater element 28 to also contribute to firm physical contact between the faces of element 28 and the plates 22 and 24.

Power is supplied to the unit by a conventional power cord 68. One lead of power cord 68 is connected to a terminal on the upper aluminum plate 22. The other lead of power cord 68 is connected to one of the contacts of thermostat 42, and the other contact of the thermostat is connected to a terminal (not shown) on plate 24. Thus, when the contacts of the thermostat are closed, an electrical circuit is completed and power is supplied to the unit, since current flows through the thermostat and between the aluminum plates 22 and 24 through PTC heater element 28. Lamp 54 is also connected to plates 22 and 24 so that the lamp is illuminated when the unit is powered.

To operate the disinfecting unit of the present invention, the user will first put the contact lenses in the lens holder with saline or other appropriate solution and place the lenses in cavity 20, as shown in FIG. 2. Cover 18 will then be closed as in FIG. 1. The user will then apply downward finger force to indicator cover 58 to move housing 56 and projection of plunger 60 downward. The downward movement of plunger 60 pushes reset button 52 downward to close the open contacts 41 and 43 of thermostat 42. Upon closing of the contacts 41 and 43, the unit is then powered, with the supply voltage being imposed across plates 22 and 24 and current flowing in the plates. The voltage across plates 22 and 24 causes a current flow and the generation of heat in thermistor 28. The heat generated in thermistor 28 is transferred to plates 22 and 24 where it is spread or distributed and then transferred to heating cavity 20. However, because of the mass of the aluminum plates 22 and 24 and plastic separator plate 26, residual heat is also stored in this plate assembly to constitute a residual heat supply for the unit after the power supply is discontinued.

Thermostat 42 is housed in block housing 38 which is both attached to plastic plate 26 and is in intimate heat exchange contact with plate extension 39 of plate 24. Plate 39 has a central opening 70 directly below the position of thermostat 42 in recess 40 of housing 38. Thus, the heat from plate 39 is not transferred directly to thermostat 42; rather, plate 39 heats housing 38 and cooperates with housing 38 to define an isothermal heat source communicating with the thermostat 42. Also, the elements of the heat supply structure are calibrated and the temperatures and the heat quantities in the various elements are balanced so that the temperature of thermostat 42 is essentially equal at all times to the temperature in chamber 20 to which the lenses are exposed.

Thermostat 42 is calibrated so that it operates to open the contacts and discontinue the power supply at a temperature which will produce a temperature of at least 80° C. (approximately 176° F.) for a period of at least 10 minutes in the lens case in cavity 20 in combination with the residual heat supply. When that temperature is reached, heat generation from the thermistor 28 will be terminated because of the interruption of power. Before that temperature is reached, however, the operating characteristic of the thermistor contributes an important operating feature to the invention. That is, the electrical resistance of the thermistor increases as the temperature to which it is exposed increases. Thus, as the temperature of the heating unit rises from ambient to the cut off temperature, the heat output of the thermistor gradually decreases so that the heat generated by the thermistor rises in a self levelling characteristic in accordance with the characteristics of the thermistor. This prevents overheating from occurring, and it also contributes to the generation of a desired amount of residual heat in the heating system to be delivered to and absorbed in the heating cavity after the power is terminated.

When thermostat 42 opens to discontinue the power supply, a residual amount of heat has been built up and stored in the residual heat source unit of the sandwiched plates. This residual heat continues to flow to cavity 20 to maintain the temperature in cavity 20, and hence the temperature of the lenses, above 80° C. for the desired period of soak time of at least ten minutes. Since the power supply has been terminated, the residual heat constitutes the only continuing source of heat supplied to chamber 20. Thus, while the lenses continue to be exposed to a temperature of at least 80° C. in the lens case, the temperature in the lens case during the soak period does not rise above 100° C. throughout the entire heat cycle of the soak time.

Figure 4:
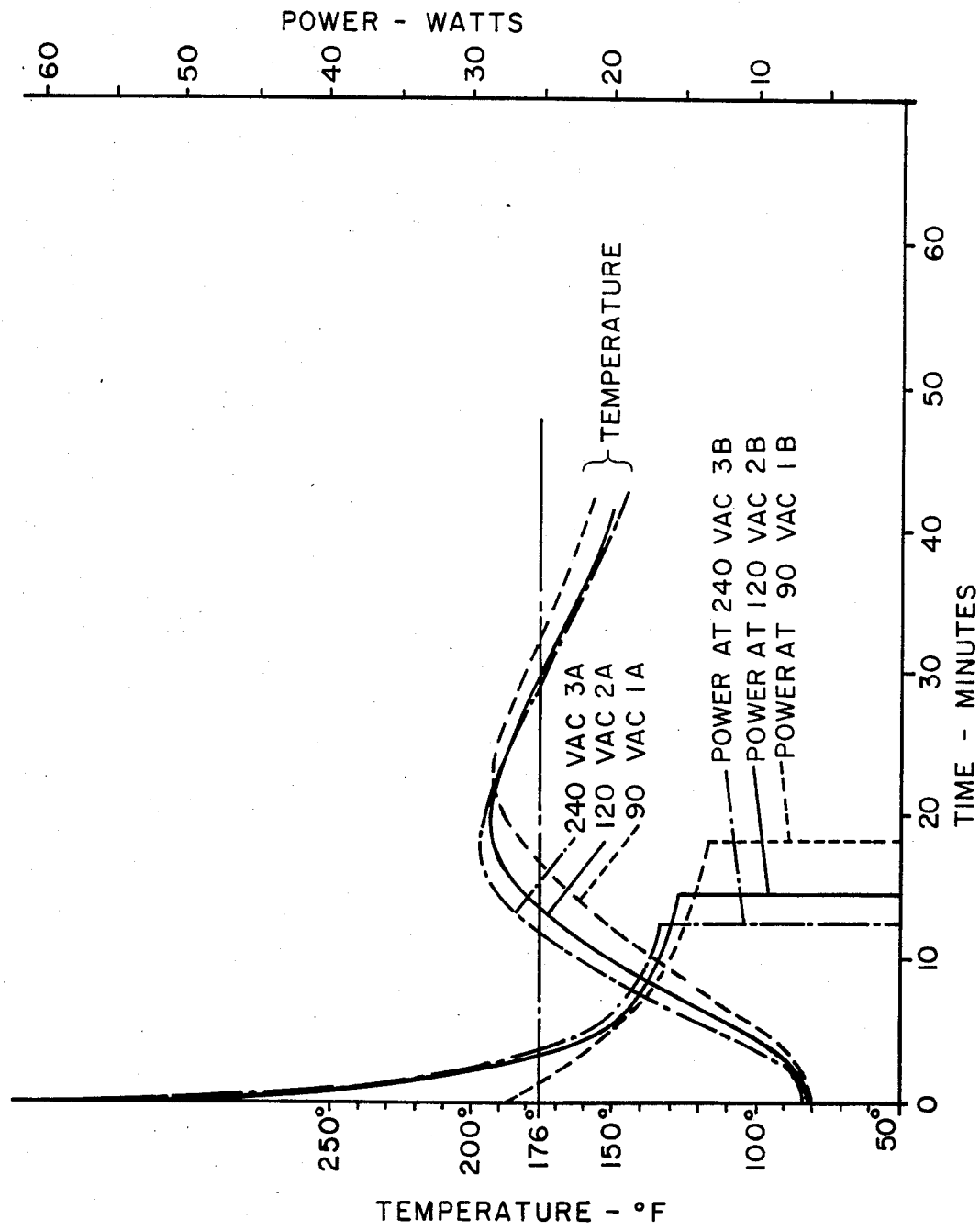
FIG. 4 is a graph showing plots of power and temperature versus time for a disinfecting unit made in accordance with the present invention.

Various tests have shown the operating characteristics and the effectiveness of the disinfecting unit of the present invention. FIG. 4 shows several of these tests in plots of power and temperature versus time. The dashed line 1A shows a plot of temperature versus time when the unit is powered with 90 volts AC, the plot of power versus time being the dashed line 1B. Similarly, lines 2A and 2B show the same plots for 120 volts AC, and lines 3A and 3B show the same plots for 240 volts AC. The data reflected by these plots is summarized in the following table:

TABLE 1

| LINES | VOLTS AC | TIME - Mins. | |
|---|---|---|---|
| | | To reach 80° C. | Dwell above 80° C. |
| 1 | 90 | 16.8 min. | 16.0 min. |
| 2 | 120 | 13.8 | 16.2 |
| 3 | 240 | 12.0 | 17.5 |

All tests were conducted at an ambient temperature of 80° F.

The charts of FIG. 4 and the results set forth in Table 1 clearly illustrate the results and advantages of the present invention. When the unit is powered at 240 volts (line 3) the temperature inside the lens case reaches the 80° C. (176° F.) soak temperature in twelve minutes; and the thermostat operates to shut off the power supply within one minute thereafter. Thereafter, heat from the heat sink structure continues to be supplied to cavity 20 so that the lens case is maintained at a temperature above the soak temperature for approximately 17.5 minutes.

With the unit operated at 120 volts power supply, the soak temperature of 80° C. (176° F.) was reached in 13.8 minutes, and the thermostat operated to discontinue the power supply within less than one minute thereafter. Heat from the residual heat source then maintained the lens case at or above the soak temperature for an additional 16.2 minutes.

With a 90 volt power supply, the 80° soak temperature was reached in 16.8 minutes, and the residual heat supply maintained the lens case at or above the soak temperature for an additional 16 minutes.

As shown in the curves of FIG. 4, the temperature of the lens at no time exceeded the upper temperature limit of 100° C. Also, the temperature curves of FIG. 4 reflect the self limiting characteristic of the thermistor. Thus, FIG. 4 shows that as the temperature rises, the rate of increase lessens during the period when the unit is powered. Thus, the unit has a self limiting characteristic even when it is powered. This self limiting characteristic provides an additional safety feature for the device in that the temperature and heat generated will be self limiting and self levelling as determined by the characteristics of the thermistor in the event that the thermostat should fail in a closed position.

While preferred embodiments have been shown and described, various modifications and substitutions may be made thereto without departing from the spirit and scope of the invention. Accordingly, it is to be understood that the present invention has been described by way of illustrations and not limitation.

What is claimed is:
1. A disinfecting unit for contact lenses including:
(a) housing defining a cavity for receiving lens to be disinfected;
(b) heating system means disposed internally of said housing for generating, storing and transferring heat to said cavity, said heating system means including:
  (i) heat generating means;
  (ii) thermostat means for controlling the delivery of supply power to said heating system;
  (iii) an generally planar insulation member having first and second portions, said first portion having an opening for receiving said heat generating means, said second portion being integral with and extending from first portion and being of greater thickness than first portion and in heat conducting relationship with said thermostat means;
  (iv) first and second electrically conductive electrode plates disposed on opposite outer surfaces of said insulation member electrically contacting said heat generating means; said first electrode plate being substantially coextensive with said first portion of said insulating member and in heat conductive contact therewith and said housing portion defining said cavity, said second electrode plate being disposed in heat exchange contact on an outer surface of both the first portion and the second portion of said insulation member for transferring heat from heat generating means to said thermostat means; and (c) circuit means for supplying power to and effectively controlling said heating system, said circuit means including said electrode plates in circuit with said thermostat means and said heat generating means thereby to de-energize said heater generating means when said thermostat means reaches a preset temperature.

2. The disinfecting unit of claim 1 wherein said thermostat means is manually resettable to energize said heat generating means.

3. The disinfecting unit of claim 1 wherein: said heat generating means is a positive temperature coefficient thermistor.

4. The disinfecting unit of claim 1 wherein the opening within the insulation member includes a plurality of sidewalls which directly contact the heat generating means.

5. The disinfecting unit of claim 1 wherein said first and second electrode plates retain said heat generating means therebetween.

6. The disinfecting unit of claim 1 wherein said second portion of the insulation member is remote from said cavity and further has a recess defined therein, wherein said thermostat means is located within said recess.

7. The disinfecting unit of claim 1 wherein said second electrode plate is coextensive with the first portion and the second portion of said insulation member.

* * * * *